United States Patent
McCormack et al.

(10) Patent No.: US 6,682,803 B2
(45) Date of Patent: Jan. 27, 2004

(54) BREATHABLE MULTILAYER FILMS WITH BREAKABLE SKIN LAYERS

(75) Inventors: Ann Louise McCormack, Cumming, GA (US); William Bela Haffner, Kennesaw, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/385,988

(22) Filed: Aug. 27, 1999

(65) Prior Publication Data

US 2002/0187304 A1 Dec. 12, 2002

(51) Int. Cl.[7] ................................................ B32B 3/26
(52) U.S. Cl. ...................... 428/138; 428/131; 428/137; 428/155
(58) Field of Search ................. 428/131, 137, 428/138, 141, 155, 317.9; 442/370

(56) References Cited

U.S. PATENT DOCUMENTS

| | | | |
|---|---|---|---|
| 3,649,404 A | 3/1972 | Waterhouse | 156/229 |
| 3,719,540 A | 3/1973 | Hall | 156/267 |
| 4,135,021 A * | 1/1979 | Patchell et al. | 428/134 |
| 4,626,252 A * | 12/1986 | Nishizawa et al. | 604/370 |
| 4,908,251 A * | 3/1990 | Iimura et al. | 428/68 |
| 5,057,097 A | 10/1991 | Gesp | 604/389 |
| 5,212,246 A | 5/1993 | Ogale | 525/240 |
| 5,272,236 A | 12/1993 | Lai et al. | 526/348.5 |
| 5,300,365 A | 4/1994 | Ogale | 428/461 |
| 5,308,904 A * | 5/1994 | Fujii et al. | 524/232 |
| 5,318,842 A | 6/1994 | Ogale | 428/349 |
| 5,322,728 A | 6/1994 | Davey et al. | 428/296 |
| 5,331,047 A | 7/1994 | Giacobbe | 525/88 |
| 5,344,691 A | 9/1994 | Hanschen et al. | 428/152 |
| 5,354,597 A | 10/1994 | Capik et al. | 428/152 |
| 5,368,927 A | 11/1994 | Lesca et al. | 428/288 |
| 5,453,318 A | 9/1995 | Giacobbe | 428/286 |
| 5,468,428 A | 11/1995 | Hanschen et al. | 264/483 |
| 5,501,679 A | 3/1996 | Krueger et al. | 604/393 |
| 5,571,619 A | 11/1996 | McAlpin et al. | 428/364 |
| 5,691,034 A | 11/1997 | Krueger et al. | 428/152 |
| 5,695,868 A | 12/1997 | McCormack | 428/283 |
| 5,885,707 A | 3/1999 | Kaschel et al. | 428/349 |
| 5,955,187 A * | 9/1999 | McCormack et al. | 428/315.5 |

FOREIGN PATENT DOCUMENTS

| | | | |
|---|---|---|---|
| EP | 367 613 | 5/1990 | B32B/27/32 |
| EP | 0 500 590 | 12/1995 | B32B/5/04 |
| EP | 862 991 | 9/1998 | B32B/3/26 |
| WO | 91/07277 | 5/1991 | B32B/5/04 |
| WO | 91/15364 | 10/1991 | B32B/25/08 |
| WO | 91/15365 | 10/1991 | B32B/25/08 |
| WO | 96/19346 | 6/1996 | B32B/7/00 |

* cited by examiner

Primary Examiner—Harold Pyon
Assistant Examiner—Alicia Chevalier
(74) Attorney, Agent, or Firm—Pauley Peterson & Erickson

(57) ABSTRACT

A breathable multilayer film including a breathable core layer and one or two skin layers is prepared by providing a core layer mixture of a thermoplastic polymer and a particulate filler, providing a skin layer mixture of at least two incompatible polymers, coextruding the core and skin layer mixtures to form a multilayer film, and stretching the multilayer film to cause void formation in the core layer and crack formation in the one or two skin layers. By forming cracks in the skin layers during stretching, the skin layers can perform dual functions of alleviating die build-up of filler from the core layer during coextrusion, and bonding the film to a substrate subsequent to coextrusion, without unduly hindering the moisture vapor transmission rate of the film or laminate product. The breathable film, and laminates including the film, are useful in a wide variety of personal care absorbent articles, medical garments, and other products.

32 Claims, 2 Drawing Sheets

BREATHABLE MULTILAYER FILMS WITH BREAKABLE SKIN LAYERS

FIELD OF THE INVENTION

This invention is directed to a breathable multilayer film having a core layer and one or two adjacent skin layers. The core layer contains a mixture of thermoplastic polymer and particulate filler, and is rendered breathable to moisture vapor when the film is stretch-thinned following coextrusion. The skin layer or layers prevent filler particles from the core layer from building up at the die lip during coextrusion. The skin layers crack and/or break during stretching to increase the breathability of the overall film.

BACKGROUND OF THE INVENTION

Breathable stretch-thinned films, and laminates including a breathable film and a nonwoven web, are used in diaper backings, other personal care products, and medical garments. U.S. Pat. No. 5,695,868, issued to McCormack, discloses a breathable film and a breathable, cloth-like film/nonwoven composite which includes the film thermally bonded to a fibrous polyolefin nonwoven web. Typically, the film includes a core layer coextruded with one or two adjacent skin layers.

The core layer, which accounts for most of the film thickness, can be formed from a mixture of a thermoplastic polymer with a substantial quantity (e.g., 30–75% by weight) of a particulate inorganic filler. When the film is stretched subsequent to coextrusion, voids form around the filler particles in the core layer. The voids are somewhat defined and separated by thin polymer membranes which permit molecular diffusion of water vapor through the film. This diffusion is what causes the film to have water vapor breathability.

The skin layer or layers account for a minor percentage of the film thickness, and may constitute less than 15% of the film thickness. The skin layers serve two main purposes. One purpose is to partially shield the die lips from the core layer during coextrusion, so that filler particles from the core layer do not excessively build up at the die lips. Another purpose is to serve as a bonding layer, which facilitates bonding of the coextruded film to a nonwoven web.

One disadvantage of skin layers is that they reduce the moisture vapor breathability of the overall film. The thicker the skin layers, the greater the reduction in breathability. Optimization of skin layer thickness requires providing enough skin layer thickness to control die build-up during extrusion and provide bonding to a nonwoven web, yet not so much skin layer thickness that overall breathability is substantially impaired. This can be a difficult balance to achieve, especially in view of the trend toward more breathable films and laminates.

SUMMARY OF THE INVENTION

The present invention is directed to a breathable, stretch-thinned film including a core layer and one or two adjacent skin layers. The core layer is made from a mixture of one or more thermoplastic polymers and a particulate filler, such that voids are formed around the filler particles when the film is stretched. The skin layers are formed from a polymer blend which maintains its integrity during coextrusion of film, yet which cracks when the film is stretched.

As a result of this invention, the skin layers can be made thick enough to adequately prevent extrusion die build-up caused by the particulate filler in the core layer. The skin layers can also be as thick as necessary to provide adequate bonding of the film to a substrate, such as a nonwoven web. Because the skin layers crack during stretching of the film, their presence does not significantly impair the moisture vapor breathability of the overall film.

The skin layer(s) are made from a blend of two or more incompatible polymers which cause cracking of the skin layer(s) when the film is stretched. In one embodiment, the skin layer(s) are made from a blend containing about 20–80% by weight branched low density polyethylene made using a conventional high-pressure polymerization process, and about 20–80% by weight of an ethylene-propylene copolymer elastomer which contains a major percentage of propylene and a minor percentage of ethylene. In another embodiment, the skin layer(s) are made from a blend containing about 20–80% by weight of an ethylene vinyl acetate copolymer containing up to about 12% by weight vinyl acetate, and about 20–80% by weight of an ethylene-propylene copolymer elastomer as described above. In another embodiment, the skin layer(s) are made from a blend containing about 20–80% by weight of an ethylene methyl acrylate copolymer, and about 20–80% by weight of an ethylene-propylene copolymer elastomer as described above.

In still further embodiments, the skin layer(s) are made from a blend containing about 75–98% by weight of a first component selected from branched low density polyethylene, ethylene vinyl acetate containing up to about 12% by weight vinyl acetate, and ethylene methyl acrylate containing up to about 12% by weight methyl acrylate; and about 2–25% by weight of a second component selected from polypropylene, polystyrene and polybutene.

The present invention also includes a method of preparing a stretch-thinned breathable film. The method includes the steps of providing a core layer composition containing one or more thermoplastic polymers and a particulate filler, providing a skin layer composition for one or both sides of the core layer, coextruding the core layer composition and skin layer composition together through a die to form a multilayer film having a core layer and at least one skin layer, stretching the film in at least one direction after it leaves the die, and cracking the skin layer during stretching of the film. An important feature of the method is that the skin layer is cracked during stretching, after it leaves the die, instead of being cracked at the die during extrusion.

With the foregoing in mind, it is a feature and advantage of the invention to provide a breathable stretch-thinned film having a core layer and a cracked skin layer on one or both sides of the core layer, the skin layer(s) being cracked during stretching of the film to provide enhanced breathability to moisture vapor.

It is also a feature and advantage of the invention to provide a breathable stretch-thinned film having improved processability, whose skin layers are thick enough to substantially prevent die build-up of particulate filler from the core layer.

It is also a feature and advantage of the invention to provide an improved method of making a multilayer stretch-thinned breathable film, in which the skin layer(s) are cracked during stretching of the film to provide enhanced breathability.

The foregoing and other features and advantages will become further apparent from the following detailed description of the presently preferred embodiments, read in conjunction with the drawings.

TEST PROCEDURE

The following procedure is described for testing of the moisture vapor transmission rate (MVTR) for the self-regulating films of the invention. The MVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGARD® 2500 (Hoechst Celanese Corporation). CELGARD 2500 is a 0.0025 cm thick film composed of microporous polypropylene. Two or three samples are prepared for each material. Test cups used for testing are cast aluminum, flanged, 5.1 centimeters deep and come with a mechanical seal and neoprene gasket. The cups are distributed by Thwing-Albert Instrument Company, Philadelphia, Pa., under the designation Vapometer cup no. 68-1. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test MVTR value is calculated as follows:

Test MVTR=[(grams weight loss over 24 hours)×7571]÷24

The relative humidity within the oven is not specifically controlled. Under predetermined set conditions of 38° C. and ambient relative humidity, the MVTR for CELGARD 2500 has been determined to be 5000 g/m$^2$-24 hours. Accordingly, CELGARD 2500 is run as a control sample with each test and the resulting values are corrected in accord with the variation of the control relative to its known MVTR.

DETAILED DESCRIPTION OF THE PRESENTLY PREFERRED EMBODIMENTS

Figure 1:
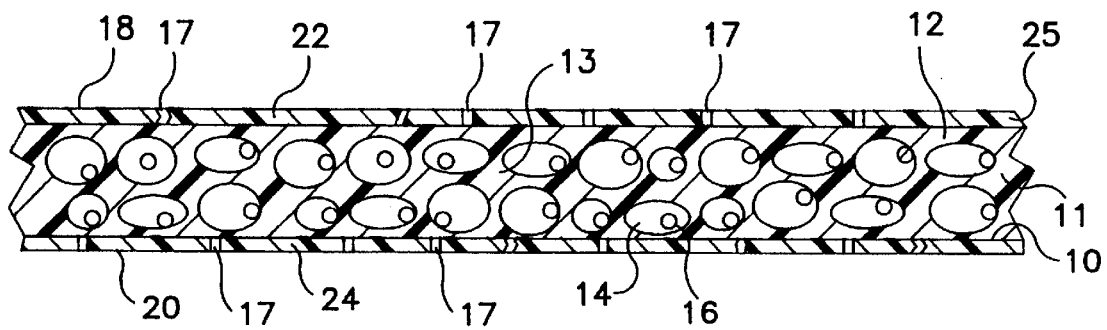
FIG. 1 is a sectional view of one embodiment of the invention, which is a three-layer breathable film.

Referring to FIG. 1, a multilayer breathable film 10 is shown including a stretch-thinned core layer 11 having a voided polymer matrix 12, sandwiched between two outer skin layers 22 and 24. The term "voided polymer matrix 12" refers to a polymer matrix which contains open spaces or "voids." Voids 14 within the matrix 12 are at least partly surrounded by thin microporous membranes 13 defining tortuous paths, and one or more filler particles 16 in each void 14. The film 10 is microporous and breathable, as defined by an MVTR of at least about 500 grams/m$^2$-24 hours. The microporous membranes 13 between the voids readily permit molecular diffusion of moisture vapor between first surface 18 and second surface 20 of the film.

The skin layers 22 and 24 include a plurality of cracks 17 which penetrate the skin layers from the outer surfaces 18 and 20 to the interfaces with core layer 11. The cracks 17 in the skin layers arise during stretch-thinning of the film 10 to cause void formation in core layer 12. Without cracking, the skin layers would inhibit some of the moisture vapor transmission that is facilitated by the void formation in polymer matrix 12. By cracking the skin layers, this inhibition can be reduced to the point where skin layers 22 and 24 do not significantly interfere with moisture vapor transmission. The result is a breathable film 10 having higher overall moisture vapor transmission rates.

Figure 2:
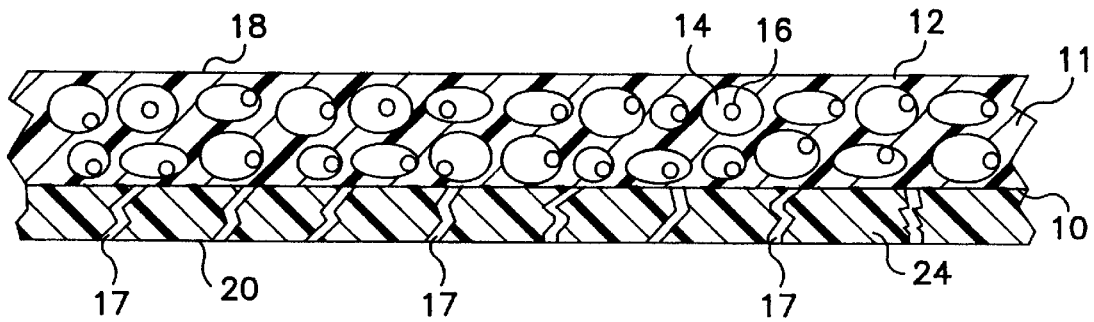
FIG. 2 is a sectional view of another embodiment of the invention, which is a two-layer breathable film.

FIG. 2 illustrates a two-layer breathable film 10 having only one skin layer 24 which is relatively thicker than the skin layers in FIG. 1. The film of FIG. 2 has a voided core layer 11 similar to the core layer shown in FIG. 1. As shown in FIG. 2, the cracks 17 penetrate all the way through the somewhat thick skin layer 24. By forming multiple cracks in skin layer 24, the breathability of the two-layer film can be maintained in spite of the thick skin layer.

Figure 3:
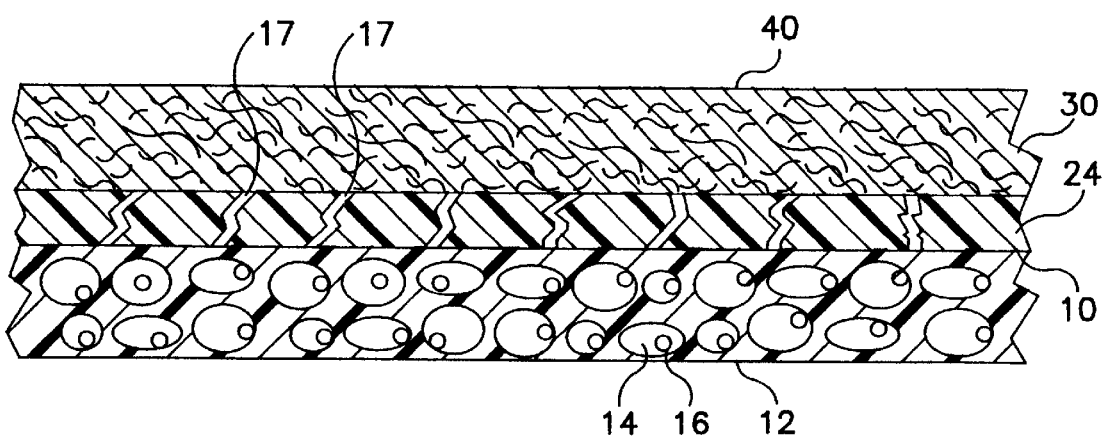
FIG. 3 is a sectional view of a laminate including a breathable film of the invention.

FIG. 3 illustrates a laminate 30 in which the two-layer film 10 of FIG. 2 is laminated by thermal bonding, adhesive bonding, ultrasonic bonding or the like, to a substrate layer 40, which can be a fibrous nonwoven web, for instance, a spunbond or meltblown web. The cracks 17 in the skin layer 24 enhance moisture vapor transmission without interfering with the bonding properties of layer 17.

The cracked skin layers, which may include a degree of fibrillation, may feel and look more clothlike than conventional breathable films without cracked surfaces. In applications where a nonwoven fabric layer might otherwise be laminated to the film to provide softness and a cloth-like feel, the cracked skin layers may provide these properties, overcoming the need for a nonwoven fabric layer.

The polymer matrix 12 defining the core layer 11 of either film 10 can be formed from any suitable film-forming thermoplastic polymer. Examples of suitable polymers include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain. Other suitable matrix polymers include without limitation elastomers, for example ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly(ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

Polymers made using metallocene catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta catalyzed polymers. It is also possible to use a metallocene catalyst system to control the isotacticity of the polymer quite closely.

Commercial production of metallocene polymers is somewhat limited but growing. Such polymers are available from Exxon Chemical Company of Baytown, Tex. under the trade name ACHIEVE® for polypropylene based polymers and EXACT® and EXCEED® for polyethylene based polymers. Dow Chemical Company of Midland, Mich. has polymers commercially available under the name AFFINITY®. These materials are believed to be produced using non-stereo selective metallocene catalysts. Exxon generally refers to their metallocene catalyst technology as "single site" catalyst while Dow refers to theirs as "constrained geometry" catalysts under the name INSITE® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade. In the practice of the instant invention, matrix polyolefins are preferred, and polyethylenes are most preferred.

The polymer matrix should constitute about 20–80% by weight of the core layer 11, preferably about 25–65% by weight, most preferably about 30–50% by weight, with the balance of the weight coming mainly from filler particles 16.

The polymer composition, filler content, filler particle size and degree of stretching are factors which help determine the breathability of the microporous core layer 11, thus influencing the breathability of multilayer film 10. Generally, the breathable film 10 will be less than about 50 microns thick, preferably less than about 30 microns thick, most preferably less than about 20 microns thick.

The filler content and degree of stretching affect the number of voids and the nature of the tortuous paths between the voids. The total filler content should range from about 20–80% by weight of the core layer 11, preferably about 35–75% by weight of the core layer 11, most preferably about 50–70% by weight of the core layer 11. The film 10 may be uniaxially or biaxially stretched. The film may be uniaxially stretched to about 1.1–7.0 times its original length, preferably to about 1.5–6.0 times its original length, most preferably to about 2.5–5.0 times its original length. The film may alternatively be biaxially stretched using conventional techniques familiar to persons skilled in the art. Stretching temperatures may range from about 38–150° C. depending on the specific polymers employed, and are generally about 70–95° C.

The filler particles 16 are preferably small, in order to maximize vapor transmission through the voids. Generally, the filler particles should have a mean particle diameter of about 0.1–7.0 microns, preferably about 0.5–7.0 microns, most preferably about 0.8–2.0 microns.

The filler particles 16 in core layer 11 may be selected from a wide variety of organic and inorganic fillers. Suitable fillers include without limitation calcium carbonate, clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. The filler particles 16 may be coated with a minor quantity (e.g. up to 2% by weight) of a fatty acid or other material to ease their dispersion in the polymer matrix. Suitable fatty acids include without limitation stearic acid, or a longer chain fatty acid such as behenic acid.

The skin layers 22 and 24 may have varying thicknesses as required for individual applications. While it is generally desirable to maximize breathability through the use of thin skin layers, the cracking of the skin layers during stretching allows more latitude for using thicker skin layers where desired. Where two skin layers 22 and 24 are employed in a three-layer film, their combined thickness may range from about 1–30% of the total film thickness, desirably about 2–15% of the total film thickness, preferably about 3–5% of the total film thickness. Each individual skin layer may have a thickness ranging from about 0.5–15% of the total film thickness, desirably about 1–7.5% of the total film thickness, preferably about 1.5–2.5% of the total film thickness. Where only one skin layer 24 is employed in a two-layer film, its thickness may constitute about 0.5–30% of the total film thickness, desirably about 1–15% of the total film thickness, preferably about 1.5–5% of the total film thickness.

The skin layers 22 and 24 crack during stretching of the film. Put another way, the skin layers maintain their integrity and should not crack during coextrusion from a die, so that they may best perform their function of minimizing die build-up of filler particles 16 from the core layer 11. The cracking of the skin layers should occur during the subsequent stretching of the film 10. The stretching imparts breathability to the film 10 both by forming voids 14 around filler particles 16 in the core layer, and by forming cracks 17 in the one or two skin layers. The cracks in the skin layers pass through the skin layers, i.e., have a depth equal to the thickness of each skin layer. The cracks 17 should have a length of at least about 0.1 mm, desirably about 0.3–10 mm, suitably about 0.5–5 mm. Also, the cracks 17 should occur at a fairly high frequency. Generally, the average distance between cracks 17 (i.e., the average distance from each crack to the nearest adjacent crack) should be less than about 10 mm, desirably less than about 5 mm, suitably less than about 1 mm.

In accordance with the invention, skin layers 22 and 24 are each constructed from two or more mildly incompatible polymers blended together. The term "mildly incompatible polymers" refers to polymers which are somewhat immiscible, and which tend to crack when in the form of a thin skin layer, when a stretching force is applied. The mildly incompatible polymers should not be so incompatible that they phase separate at the die lip, causing melt fracture or cracking at the die. Instead, the polymer blend which constitutes the skin layers should flow smoothly through the die, and maintain enough continuity to minimize die build-up from filler particles in the core layer. Yet the polymers should be sufficiently incompatible to result in separation and cracking in the skin layers when the multilayer film is stretched using the conditions set forth above, and the process described below.

In some embodiments, the skin layers can include from about 20–80% by weight of a first polymer selected from branched low density polyethylene made using a conventional high-pressure (25,000–50,000 psi) polymerization process, ethylene vinyl acetate copolymer containing up to about 12% by weight vinyl acetate, and ethylene methyl acrylate copolymer. The branched low density polyethylene can have a density of about 0.910–0.925 grams/cm$^3$, a branching level of about 15–30 equivalent methyl groups per 1000 carbon atoms, and a melting point of about 110–120° C. The ethylene vinyl acetate copolymer can be made using a similar high pressure process, and preferably contains less than about 8% by weight vinyl acetate, more preferably less than about 5% by weight vinyl acetate.

The skin layers may also include about 20–80% by weight of a second polymer which is an ethylene-propylene copolymer elastomer containing a major percentage of propylene and a minor percentage of ethylene. Suitable second polymers include heterophasic propylene-ethylene polymers, for instance, heterophasic reactor blends of a) a polypropylene homopolymer or random copolymer with up to about 10% ethylene, b) a propylene-ethylene random copolymer containing about 20–40% ethylene, and c) a propylene-ethylene random copolymer containing over 55% ethylene. Heterophasic propylene-ethylene polymers are described in U.S. Pat. No. 5,453,318, issued to Giacobbe; U.S. Pat. No. 5,368,927, issued to Lesca et al., U.S. Pat. No. 5,331,047, issued to Giacobbe; U.S. Pat. No. 5,318,842, issued to Ogale; U.S. Pat. No. 5,300,365, issued to Ogale; and U.S. Pat. No. 5,212,246, issued to Ogale; the disclosures of which are incorporated by reference.

In the foregoing embodiments, the skin layers preferably include about 30–70% by weight of each of the first and second components, more preferably about 40–60% by weight of each of the first and second components.

In other embodiments, the skin layers can include about 75–98% by weight of a first component selected from branched low density polyethylene, ethylene vinyl acetate with up to about 12% by weight vinyl acetate, and ethylene methyl acrylate; and about 2–25% by weight of a second component selected from polypropylene, polystyrene and polybutene. In these embodiments, the skin layers preferably include about 80–97% by weight of the first component and about 3–20% by weight of the second component, more preferably about 90–95% by weight of the first component and about 5–10% by weight of the second component.

The skin layers 22 and 24 should be as thick as is reasonably necessary to provide the dual functions of alleviating filler die build-up during coextrusion, and later bonding the film 10 to a substrate. Otherwise, the skin layers should be as thin as possible, so that the breathable core layer 11 may heavily influence and/or control the breathability of the multilayer film 10. The overall film 10 should have a moisture vapor transmission rate ("MVTR") of at least about 500 grams/m$^2$-24 hours, measured using the procedure described above. Preferably, the film 10 should have an MVTR of at least about 1500 grams/m$^2$-24 hours, more preferably at least about 3000 grams/m$^2$-24 hours.

Figure 4:
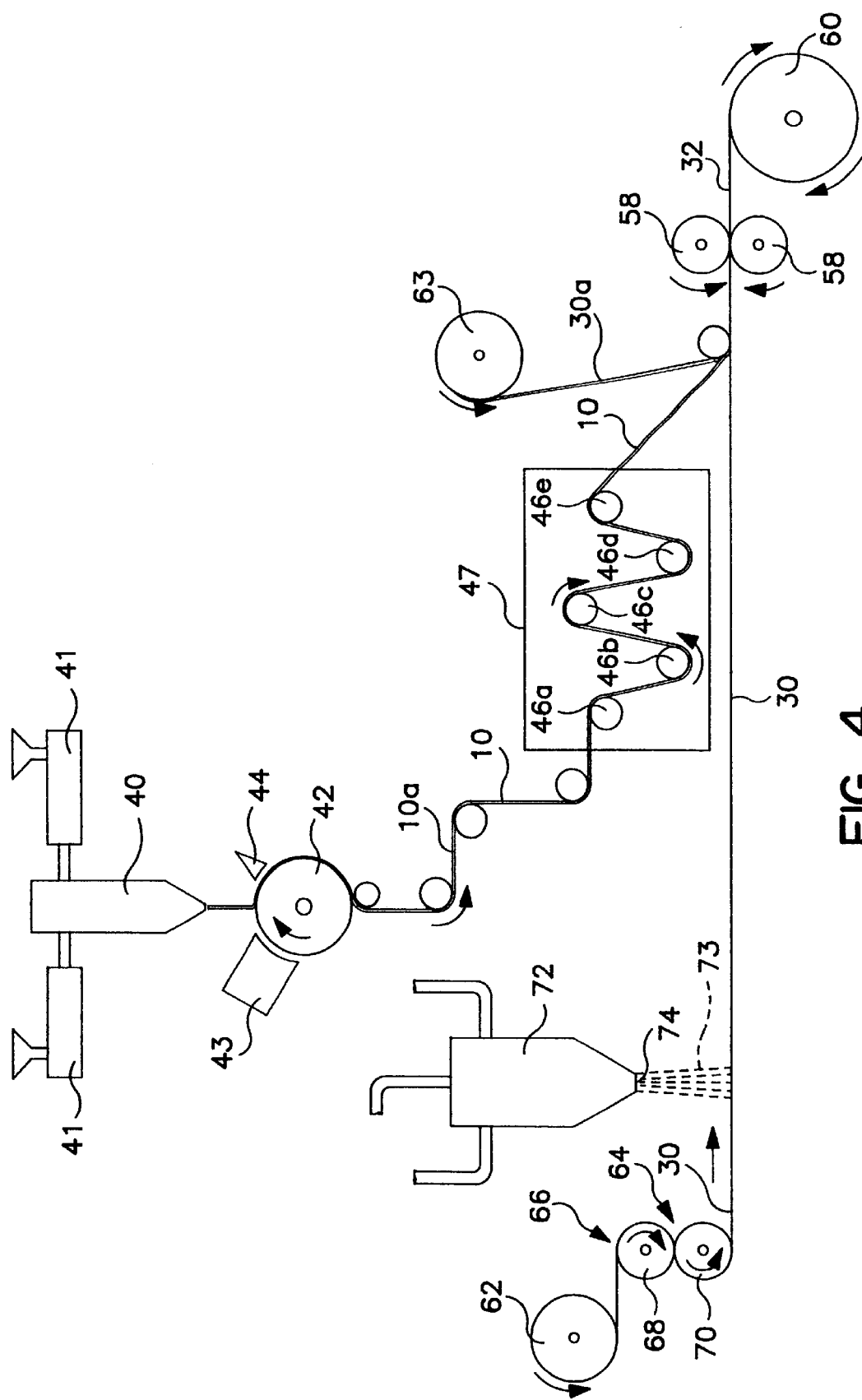
FIG. 4 is a schematic diagram of an integrated process for making a breathable film and laminate of the invention.

FIG. 4 illustrates an integrated process for forming a multilayer breathable film and a laminate. Referring to FIG. 4, film 10 is formed from a film coextrusion apparatus 40 such as a cast or blown unit which could be in-line or off-line. Typically the apparatus 40 will include two or three extruders 41. To make the core layer, filled resin including the polymer matrix material and filler is prepared in a mixer (not shown) and directed to an extruder 41. To make each skin layer, similar additional mixing apparatus (not shown) and extrusion apparatus 41 can be used to mix the incompatible polymer components and extrude them as skin layers on one or both sides of the core layers. The multilayer film 10 is extruded onto a chill roller 42, which may be patterned so as to impart an embossed pattern to the newly formed film 10. The film is cooled on the chill roller 42. A vacuum box 43 adjacent the chill roller creates a vacuum on the surface of the chill roller to help maintain the film close to the surface of the chill roller. Air knives or electrostatic pinners 44 also urge the film 10 against the roller surface.

From the film extrusion apparatus 40 or off-line rolls supplied, the multilayer film 10 is directed to a film stretching unit 47 which can be a machine direction orienter, commercially available from vendors including the Marshall and Williams Co. of Providence, R.I. Apparatus 47 has a plurality of stretching rollers 46a–e, which progressively stretch and thin the film in the machine direction, which is the direction of travel of the film. The rollers 46a–e, which are heated to the desired stretching temperature, apply an amount of stress and progressively stretch the multilayer film 10 to a stretched length where the core layer 11 becomes microporous and breathable, and the skin layers 22 and 24 become cracked as explained above. While the apparatus 47 is shown with five stretching rollers 46a–e, the number of rollers may be greater or less depending on the level of stretch desired and the amount of stretching between each pair of rollers.

Advantageously, the film 10 may be uniaxially stretched to about 1.1–7.0 times its original length, preferably about 2–6 times its original length, suitably about 3–5 times its original length, using an elevated stretch temperature of about 38–150° C., preferably about 70–95° C. for most polyolefin-based films. The elevated stretch temperature can be sustained by heating some or all of the stretch rollers 46a–e. The optimum stretch temperature varies with the core layer and skin layer polymers film 10, and is generally below the melting temperature of the matrix polymer in the core layer 11.

The multilayer film 10 may be laminated to one or more substrates, such as a nonwoven web, using conventional adhesive bonding or thermal bonding techniques known in the art. The type of substrate and bonding will vary depending on the particular end use application. Referring again to FIG. 4, film 10 may be laminated to nonwoven web 30 immediately after the film is stretched. In one embodiment, a neckable nonwoven web 30, which can be a spunbond web, is unwound from a supply roll 62. The neckable material 30 then passes through the nip 64 of S-roll arrangement 66, formed by a stack of rollers 68–70, in a reverse S-wrap path as shown by the arrows. Rollers 68 and 70 turn at a slower circumferential speed than downstream calender bonding rollers 58, causing tensioning and neck-in of web 30. The tensioned, necked material can be passed under spray equipment 72 which sprays adhesive 73 through die head 74 onto a surface of web 30. With or without the adhesive treatment, the necked web 30 can then be joined to multilayer film 10 and bonded between calender rollers 58, which can be heated if necessary. The film 10 in FIG. 4 is simultaneously bonded on its other side to a second material 30a originating from supply roll 63. The second material 30a may be a second nonwoven web, or another film layer. The resulting laminate 32 is wound and stored on a supply roll 60.

The resulting breathable laminate may be used in a wide variety of personal care absorbent articles and medical articles. Absorbent articles include without limitation diapers, training pants, swim wear, absorbent underpants, adult incontinence products, feminine hygiene products, and the like. Medical products include medical garments, underpads, bandages, drapes, medical wipes, and the like.

Other examples of laminates and end uses in which the self-regulating film may be useful are described in various patents and patent applications assigned to Kimberly-Clark Worldwide, Inc. These include without limitation U.S. application Ser. No. 08/359,986, filed Dec. 20, 1994; U.S. application Ser. No. 08/755,692, filed Nov. 25, 1996; and U.S. application Ser. No. 08/777,365, filed Dec. 27, 1996. These patent applications are incorporated herein by reference in their entirety.

While the embodiments of the invention disclosed herein are presently considered preferred, various modifications and improvements can be made without departing from the spirit and scope of the invention. The scope of the invention is indicated by the appended claims, and all changes that fall within the meaning and range of equivalents are intended to be embraced therein.

We claim:

1. A breathable film comprising a core layer and a skin layer on both sides of the core layer;
   the core layer including a mixture of one or more thermoplastic polymers and filler particles, with voids around the filler particles;
   each skin layer including about 20–80% by weight of a first incompatible polymer and about 20–80% by weight of a second incompatible polymer, and having a plurality of cracks passing through the skin layer formed therein by stretch-thinning the film, thereby reducing moisture vapor transmission inhibition;
   wherein a total skin layer thickness is about 30% or less of a total film thickness.

2. The breathable film of claim 1, wherein the second incompatible polymer comprises an ethylene-propylene copolymer elastomer containing a major percentage of propylene and a minor percentage of ethylene.

3. The breathable film of claim 2, wherein the first incompatible polymer comprises branched low density polyethylene.

4. The breathable film of claim 2, wherein the first incompatible polymer comprises an ethylene vinyl acetate copolymer containing up to about 12% by weight vinyl acetate.

5. The breathable film of claim 2, wherein the first incompatible polymer comprises an ethylene methyl acrylate copolymer.

6. The breathable film of claim 1, wherein the skin layers on both sides of the core layer comprise about 30–70% by weight of the first incompatible polymer and about 30–70% by weight of the second incompatible polymer.

7. The breathable film of claim 1, wherein the skin layers on both sides of the core layer comprise about 40–60% by weight of the first incompatible polymer and about 40–60% by weight of the second incompatible polymer.

8. A breathable, stretch-thinned film comprising a core layer and a skin layer on both sides of the core layer;
   the core layer including a mixture of one or more thermoplastic polymers and filler particles, with voids around the filler particles;
   each skin layer including about 75–98% by weight of a first incompatible polymer and about 2–25% by weight of a second incompatible polymer, and having a plurality of cracks passing through the skin layer formed therein by stretch-thinning the film, thereby reducing moisture vapor transmission inhibition;
   wherein a total skin layer thickness is about 30% or less of a total film thickness.

9. The breathable film of claim 8, wherein the first incompatible polymer comprises branched low density polyethylene and the second incompatible polymer comprises polypropylene.

10. The breathable film of claim 8, wherein the first incompatible polymer comprises branched low density polyethylene and the second incompatible polymer comprises polystyrene.

11. The breathable film of claim 8, wherein the first incompatible polymer comprises branched low density polyethylene and the second incompatible polymer comprises polybutene.

12. The breathable film of claim 8, wherein the first incompatible polymer comprises ethylene vinyl acetate containing up to about 12% by weight vinyl acetate, and the second incompatible polymer comprises polypropylene.

13. The breathable film of claim 8, wherein the first incompatible polymer comprises ethylene vinyl acetate containing up to about 12% by weight vinyl acetate, and the second incompatible polymer comprises polystyrene.

14. The breathable film of claim 8, wherein the first incompatible polymer comprises ethylene vinyl acetate containing up to about 12% by weight vinyl acetate, and the second incompatible polymer comprises polybutene.

15. The breathable film of claim 8, wherein the first incompatible polymer comprises ethylene methyl acrylate, and the second incompatible polymer comprises polypropylene.

16. The breathable film of claim 8, wherein the first incompatible polymer comprises ethylene methyl acrylate, and the second incompatible polymer comprises polystyrene.

17. The breathable film of claim 8, wherein the first incompatible polymer comprises ethylene methyl acrylate, and the second incompatible polymer comprises polybutene.

18. The breathable film of claim 8, wherein the skin layers on both sides of the core layer comprise about 80–97% by weight of the first incompatible polymer and about 3–20% by weight of the second incompatible polymer.

19. The breathable film of claim 8, wherein the skin layers on both sides of the core layer comprise about 90–95% by weight of the first incompatible polymer and about 5–10% by weight of the second incompatible polymer.

20. A breathable film comprising a core layer and a skin layer on both sides of the core layer;
   the core layer including a mixture of one or more thermoplastic polymers and filler particles, with voids around the filler particles;
   each skin layer including about 20–98% by weight of a first incompatible polymer and about 2–80% by weight of a second incompatible polymer, and having a plurality of cracks passing through the skin layer formed therein by stretch-thinning the film, thereby reducing moisture vapor transmission inhibition;
   wherein a total skin layer thickness is about 30% or less of a total film thickness.

21. A breathable laminate comprising the film of claim 20 and a fibrous nonwoven web.

22. A diaper comprising the laminate of claim 20.

23. A training pant comprising the laminate of claim 20.

24. Swim wear comprising the laminate of claim 20.

25. An absorbent underpant comprising the laminate of claim 24.

26. An adult incontinence product comprising the laminate of claim 20.

27. A feminine hygiene product comprising the laminate of claim 20.

28. A medical garment comprising the laminate of claim 20.

29. An underpad comprising the laminate of claim 20.

30. A bandage comprising the laminate of claim 20.

31. A medical drape comprising the laminate of claim 20.

32. A medical wipe comprising the laminate of claim 20.

* * * * *